US009795593B2

(12) United States Patent
Khmelshchikov et al.

(10) Patent No.: US 9,795,593 B2
(45) Date of Patent: Oct. 24, 2017

(54) USE OF 3-(3-[1,2,4]-TRIAZOLO)-OXATRIAZOLIUM-5-OLATE FOR TREATING SEXUAL DISORDERS

(71) Applicant: LIMITED LIABILITY COMPANY "KONSORTSIUM-PIK", Moscow (RU)

(72) Inventors: Yuri Vladimirovich Khmelshchikov, Moscow (RU); Dmitriy Sergeevich Noskov, Moscow (RU)

(73) Assignee: LIMITED LIABILITY COMPANY "KONSORTSIUM-PIK", Moscow (RU)

( * ) Notice: Subject to any disclaimer, the term of this patent is extended or adjusted under 35 U.S.C. 154(b) by 0 days.

(21) Appl. No.: 15/323,567

(22) PCT Filed: Jul. 1, 2015

(86) PCT No.: PCT/RU2015/000413
§ 371 (c)(1),
(2) Date: Mar. 29, 2017

(87) PCT Pub. No.: WO2016/003327
PCT Pub. Date: Jan. 7, 2016

(65) Prior Publication Data
US 2017/0202809 A1 Jul. 20, 2017

(30) Foreign Application Priority Data

Jul. 4, 2014 (RU) ................................ 2014127279

(51) Int. Cl.
*A61K 31/4196* (2006.01)
(52) U.S. Cl.
CPC ................................ *A61K 31/4196* (2013.01)
(58) Field of Classification Search
CPC ................................................. A61K 31/4196
USPC ........................................................ 514/361
See application file for complete search history.

(56) References Cited

U.S. PATENT DOCUMENTS

| 5,091,398 A | 2/1992 | Schonafinger et al. |
| 7,135,474 B2 | 11/2006 | Weigand et al. |
| 2005/0113409 A1 | 5/2005 | Connor et al. |
| 2012/0277200 A1 | 11/2012 | Tuiten et al. |

FOREIGN PATENT DOCUMENTS

| EP | 0392233 A1 | 10/1990 |
| RU | 2351328 C1 | 4/2009 |
| WO | 2006/055542 A2 | 5/2006 |
| WO | 2008/087177 A1 | 7/2008 |
| WO | 2011/161655 A1 | 12/2011 |
| WO | 2013/100340 A1 | 7/2013 |

OTHER PUBLICATIONS

Furchgott, et al., "The Obligatory Role of Endothelial Cells in the Relaxation of Arterial Smooth Muscle by Acetylcholine". Nature, Nov. 27, 1980; 288(5789):373-376 (Abstract).
Ageev, F.T., Ovchinnikov, A.G., Mareev, V.Yu., Belenkov, Yu.N. Endothelial dysfunction and heart failure: pathogenetic relations and possibility of treatment with the use of angiotensin-converting enzyme // Consilium medicum, vol. 3, No. 2, 2001.—media/consilium/01_02/61.shtml :: sunday, Apr. 22, 2001 15:01:07.
Staroseltseva, O.A. Use of pharmacological preconditioning with Nicorandil . . . Author's dissertation abstract . . . Candidate of Medical Sciences, Kursk.—2012.
Bivalacyna T.I., Usta M.F., Champion H.C. et al. // I. Androl.—2003—V.24, No. 6.—p. 17-37. (Statement of Relevancy only).
Solomon H., Man J.M., Jackson G. // Heart.—2003.—V. 89.—p. 251-253.
Pyrochkin, V.M., Mironchik, E.V. Erectile dysfunction: new symptom for cardiologist? // Meditsinskie novosti. No. 10, 2010.—www.mednovosti.by.
T.L. Thomas, M. Fedorchuk, B.V. Shetty, E.E. Amderson. <<The Synthesis and Activity of Some 3-Substituted 1,2,3,4-Pseudooxatriazol-5-ones and Their Precursors and Related Compounds>> // Pennwalt Corporation, Pharmaceutical Division, Department of Organic Chemistry, Rochester, New York, Nov. 8, 1969.
Mary Q. Lund, Lemont B. Kier, Richard A. Glennon, John L. Egle, Jr. <<Preliminary Studies of Mesoionic 3-(Substituted-aryl)-ψ-oxatriazoles as Potential Antihypertensive Agents>> // Department of Pharmaceutical Chemistry, School of Pharmacy, and Department of Pharmacology, Medical College of Virginia, Virginia Commonwealth University, Richmond, Virginia 23298, Dec. 4, 1982.
Medical laboratory technologies. vol. 2. Prof. A.I. Karpishchenko (ed.)—SPb: Intermedica, 2002,—600 pp. (Statement of Relevancy only).
Menshikov, V.V. Clinical laboratory analytics: vol. 1, vol. 2. Special analytical technologies in the clinical laboratory.—M.: Labirinform—RAMLD, 1999. 352 pp., in 2 vol. (Statement of Relevancy only).
Bairamov, A.A., Zaichenko, I.N., Bogdanovca, L.A., Sapronov, N.S. Role of cholinergic pathways in the regulation of sexual activity in the acute and chronic stress // Farmakologiya, vol. 7, 2006. p. 18-28. (with English-language Abstract).
Buresh, Ya., Bureshova, O., Houston, D.P. Methods and main experiments in the studies of brain and behaviour./ Batuev, A.S. (ed.).—M.: Vysshaya shkola, 1991. 399 pp. (Statement of Relevancy only).
Glanz S. Medico-biological statistics.—M.: Praktika, 1998. 459 pp.(Statement of Relevancy only).
Statistics: Statistica 6.0 (Company guideline) StatSoft, 1999. 3756 pp. (Statement of Relevancy only).

(Continued)

*Primary Examiner* — Taofiq A Solola
(74) *Attorney, Agent, or Firm* — Brundidge & Stanger, P.C.

(57) ABSTRACT

The invention belongs to the chemical and pharmaceutical industry, including the creation of a new medicinal agent intended to treat sexual disorders, and can be used in the biochemistry, physiology and medicine.

2 Claims, 3 Drawing Sheets

(56) References Cited

OTHER PUBLICATIONS

International Search Report and Written Opinion from International Application No. PCT/RU2015/00413 dated Nov. 5, 2015.
Radchenko, A.D., "Hypertension" 3(23) 2012, 8 pages.
Miller, Loan N., "A-350619: A Novel Activator of Soluble Guanylyl Cyclase", Life Sciences 72 (2003) 1015-1025.
Artemyeva, et al., "Cardiovascular System Pharmacology", Experimental and Clinical Pharmacology, 2012 vol. 75 No. 8 pp. 11-14.
S.A. Shevelev, et al., "Synthesis of Mesoionic 3-Aryl(Hetaryl)-1,2,3,4-Oxatriazolones-5 Based on N-Aryl- and N-Hetarylhydrazones of Bromonitroformaldehyde", Heteroringic Chemistry—1999—No. 3—p. 413-424.

USE OF 3-(3-[1,2,4]-TRIAZOLO)-OXATRIAZOLIUM-5-OLATE FOR TREATING SEXUAL DISORDERS

The group of inventions belongs to the chemical and pharmaceutical industry, including the creation of a new medicinal agent intended to treat sexual disorders, and can be used in the biochemistry, physiology and medicine.

BACKGROUND OF THE INVENTION

The independent role of vascular endothelium in the regulation of vascular tone was firstly stated in Furchgott and Zawadzki article published in Nature, 1980. The authors revealed the ability of independent muscular tone changes in the isolated artery in response to acetylcholine, without participation of central (neuro-humoral) mechanisms.

Further studies confirm that endothelium is not a passive barrier between the blood and the tissues, but an active structure. Its dysfunction is inherent in the pathogenesis of almost any cardiovascular disorders, including atherosclerosis, hypertension, coronary heart disease (CHD), chronic heart failure (CHF). Moreover, it participates in the inflammatory reactions, autoimmune processes, diabetes, thromboses, sepsis, malignant growth etc. [1].

Normally, endothelial reaction consists in the increased production of substances that lead to the relaxation of smooth muscles of the vascular wall, primarily of nitric oxide (NO) and its derivatives (endothelial relaxation factors), together with prostacyclin and endothelium-dependent hyperpolarization factor. It should be noted that NO effects are not limited by local dilation, but include anti-proliferative effect on the vascular smooth muscles. Moreover, NO exerts several important systemic effects within the vascular lumen, including those protecting the vascular walls and preventing clots formation: blockade of platelet aggregation, of low-density lipoprotein (LDL) oxidation, of adhesion molecules expression, of monocytes and platelets adhesion to the vascular wall, of endothelin production. In certain cases, endothelium becomes a cause of vascular constriction, both due to reduced NO production and to the increased synthesis of vasoconstrictors (endothelial constriction factors): over-oxydized anions, vasoconstrictor prostenoids like thromboxane A2, and endothelin-1 (ET-1). Prolonged exposure to various damaging factors (hypoxia, intoxication, inflammation, haemodynamic overload) results in the gradual depletion and inversion of compensatory dilatation ability of endothelium, and predomination of vasoconstriction and endothelial proliferation in response to the usual stimuli. Chronic excessive activation of renin-angiotensin-aldosterone system (RAAS) is a most important factor of endothelial dysfunction. [1]

Nitric oxide molecule (NO) is a principal vasodilating agent. Normally, low levels of NO are continuously released from the endothelium and supports the dilatation of the vessels. Search of efficacious methods of correction of impaired endothelial functions in CHD patients is one of the important goals of modern cardiology. In this context, both experimental and practical medicine express interest to the studies of a physiological phenomenon named "preconditioning". Preconditioning as a result of short episodes of ischemia-reperfusion leads to improved tissue resistance to ischemia. Various methods of preconditioning are available. Clinically, pharmacological preconditioning is preferable due to technological simplicity and absence of potential ischaemic danger for affected tissues. Among pharmacological substances, Nicorandil is one of the most promising humoral agents that take part in the implementation of preconditioning phenomenon. Nicorandil possesses favourable properties, such as the absence of adverse effects. Moreover, it is one of nitric oxide donators [2].

Staroseltseva O. A. et al. demonstrated significant endothelial and cardiac protection due to ischaemic preconditioning in the model of L-NAME-induced NO deficiency. This protection manifested in the reduction of endothelial dysfunction ratio (EDR) to 2.5±0.3 AU, prevention of NO level depression (4.8±0.29 mcmol/L) and of CRP increase (0.74±0.05 mg/dL), prevention of excessive adrenergic reactivity, and in the increase of cardiac contractility up to 87.1±6.4% during resistance testing; Nicorandil (4 mg/kg) preconditioning resulted in significant endothelial and cardiac protection in the model of L-NAME-induced NO deficiency, which resulted in EDR reduction to 1.76±0.18 AU, complete prevention of NO level reduction (6.2±0.25 mcmol/L) and of CRP increase (0.6±0.1 mg/dL), prevention of excessive adrenergic reactivity and increased myocardium contractility up to 77.2±8.3% during resistance testing. Pathomorphological studies revealed decreased occurrence of membranous glomerulopathy, cardiac myocyte hypertrophy and necrosis of cardiomyocytes, destructive changes of vascular endothelium and hypertrophy of vascular walls in the kidneys and in the myocardium. Glibenclamide (4 mg/kg) provided blockade of ATP-dependent potassium channels and neutralized protective effects of distant ischaemic preconditioning on the endothelium and on the heart, as well as of helium (inert gas) preconditioning, of pharmacological preconditioning with the use of Nicorandil in the model of L-NAME-induced NO deficiency. This resulted in EDR increase up to the values close to those in L-NAME group, in NO decrease and in the increase of C-reactive protein in any groups [2].

NO-synthase blockade due to 7-day-long administration of L-NAME is known to induce arterial hypertension (mean systolic blood pressure 191.3±7.1, mean diastolic BP 146.0±4.2 mm Hg) and 5-fold increase of endothelial dysfunction ratio. The effect of concomitant use of NO donator, L-arginine, and arginase inhibitors L-norvaline and nor-NONA, leading to the neutralization L-NAME-induced endothelial dysfunction, was demonstrated and resulted in EDR and blood pressure reduction. The most efficacious combination included L-arginine 70 mg/kg and L-norvaline 10 mg/kg in the longed-acting form with 12-hour release period.

One of the main physiological mechanisms of smooth muscle relaxation consists in the increase of cGMP (cyclic nucleotide) level. At present, NO-cGMP-dependent pathway of vascular relaxation is well studied. This pathway is mediated by the activation of soluble guanylate cyclase (sGC). Here, the drugs are used that are able to produce NO. This leads to rapid increase of cGMP level in the vascular smooth muscles for a short time. However, repeated NO-donator use leads to desensitization of NO-cGMP-dependent pathway and to the tolerance that results in their inefficacy in cases of long-term administration. Therefore, the search of mechanisms and drugs capable to activate sGC for a long time is one of the promising concepts in the physiology and pharmacology of cardiovascular system. In 1966, the hypotensive effect of oxatriazole derivatives in anaesthetized dogs was revealed. The mechanism of hypotensive effect of oxatriazolium-5-olate was not investigated.

One of oxatriazolium-5-olate derivatives, 3-(3-[1,2,4]-triazolo)-oxatriazolium-5-olate (AS-6), provides prolonged hypotensive effect in conscious SHR and Wistar rats. In the present study, the level of activation of purified sGC obtained of the rabbit's lungs, was examined for the purpose of assessing the biochemical mechanism of AS-6 effects. In vitro, AS-6 (100 mcmol/L) activates sGC up to 30-fold compared to the basal activity. sGC activation increases following AS-6 level increase, therefore, this effect is dose-dependent. Moreover, AS-6 provides activation of cGMP synthesis in the aorta of Wistar rats up to 13-fold level compared to baseline. Thus, AS-6 stimulated cGMP synthesis induced both by purified sGC and sGC in the aortic tissue. sGC activation is dose-dependent [3].

Recently, a significant importance is attributed to endothelial dysfunction as a possible cause of erectile dysfunction [4, 5]. This phenomenon leads to the loss of regulatory properties of endothelium, primarily of the ability to change the smooth muscle tone at the boundary of endothelium due to the local decrease of NO production. The key role of increased NO discharge in the start, development, and maintenance of erection is well established [6].

Moreover, the pharmaceutical agents used for improving sexual potency, are known [7].

However, such pharmaceutical agents cannot be used solely for the treatment of sexual disorders, and are applied for prophylactic purposes.

A pharmaceutical agent that improves sexual potency is available [8].

This pharmaceutical agent is rather used as required, and its administration is not for treatment purposes.

The closest analogue represents a pharmaceutical agent used to treat the sexual disorders [9].

However, this agent does not provide effective local NO production and any hypotensive effect, therefore, cannot be effective in the treatment of sexual disorders.

SUMMARY OF THE INVENTION

In the context of the above facts, the purpose of the present invention consists in the creation of a new pharmaceutical agent providing efficacious treatment of sexual disorders.

The technical result of this invention consists in the expansion of the sphere of use of 3-(3-[1,2,4]-triazolo)-oxatriazolium-5-olate.

Another technical result of this invention consists in the creation of pharmaceutical composition providing efficacious treatment of sexual disorders.

This technical result can be obtained due to the use of 3-(3-[1,2,4]-triazolo)-oxatriazolium-5-olate as a treatment of sexual disorders as a part of pharmaceutical composition intended for treatment of sexual disorders.

The embodiment of this invention concern the use of 3-(3-[1,2,4]-triazolo)-oxatriazolium-5-olate as a treatment of sexual disorders and the pharmaceutical composition intended to treat sexual disorders that contains 3-(3-[1,2,4]-triazolo)-oxatriazolium-5-olate.

EMBODIMENTS OF INVENTION

Figure 1:
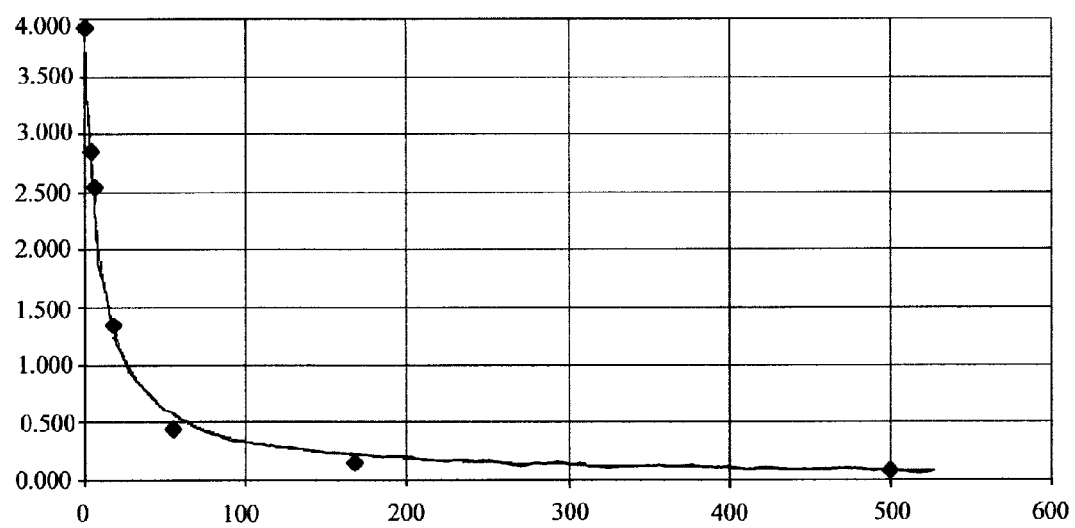
FIG. 1—Dependency diagram of endothelin-1 (ET-1) absorption vs. analyte concentration.

Correspondingly, one of the modes of implementation of the present invention consists in the use of at least one pharmaceutically acceptable 3-(3-[1,2,4]-triazolo)-oxatriazolium-5-olate in the treatment of sexual disorders.

Another embodiment of this invention concerns the use of 3-(3-[1,2,4]-triazolo)-oxatriazolium-5-olate in the treatment of sexual disorders characterizing by the selection of sexual disorders of the following series: absence or loss of sexual desire, insufficient genital reaction, orgasmic dysfunction.

Another embodiment of this invention concerns the pharmaceutical composition for treatment of sexual disorders that contains at least 3-(3-[1,2,4]-triazolo)-oxatriazolium-5-olate as an active ingredient in the dose necessary for achieving therapeutic effect.

Another embodiment of this invention concerns the pharmaceutical composition for treatment of sexual disorders that contains at least 3-(3-[1,2,4]-triazolo)-oxatriazolium-5-olate as an active ingredient in the dose necessary for achieving therapeutic effect, characterizing by the selection of sexual disorders of the following series: absence or loss of sexual desire, insufficient genital reaction, orgasmic dysfunction.

Another embodiment of this invention consists in the use of 3-(3-[1,2,4]-triazolo)-oxatriazolium-5-olate as an active ingredient of the pharmaceutical composition in the dose 0.005 g to 0.116 g.

SUMMARY OF THE INVENTION

The synthesis of pharmaceutical compositions containing at least one pharmaceutically acceptable oxatriazolium-5-olate derivative, is based on the state of the art and does not need a detailed description. These compositions can be obtained with the use of known technologies (such as tabletization) and can be present in any state-of-the-art pharmaceutical form (i.e., tablets, liquid forms, capsules).

In order to control the accuracy and applicability of the present technical invention, the research study was launched aimed to assess the specific pharmacological activity of the compounds. Further results will be presented with the example of 3-(3-[1,2,4]-triazolo)-oxatriazolium-5-olate (Azasidnon, AS-6).

Based on the article 11 of the Federal Law "About pharmaceutical circulation" (#61-FZ), "Preclinical evaluation of the medicinal agents is performed based on the scientific methods of assessment for the purposes of obtaining the evidences of safety, quality and efficacy of medicinal agents".

The abbreviations used in the text are the following:
ET-1—rat endothelin-1
L-NAME—N-omega-nitro-L-arginine methyl ester hydrochloride
NO—nitric oxide
NO—nitric oxide, free
VEGF—vascular endothelial growth factor
AH—arterial hypertension
IG—intragastric administration mode
DBP—diastolic blood pressure
MLP—mounting latency period
RAAS—Renin Angiotensin Aldosterone System
SBP—systolic blood pressure
HR—heart rate
ED—endothelial dysfunction.

Materials and Methods of the Research Study

Materials and Methods Used to Assess the Specific Activity of AS-6 in the Experimental Model of Arterial Hypertension with Endothelial Dysfunction In the model of arterial hypertension with endothelial dysfunction, endothelial NOS blocker N-nitro-L-arginine methyl ester (L-NAME) was administered intraperitoneally, 25 mg/kg, daily, for 7 days [2, 3]. The blocker was administered in 3% sodium chloride in the dose 1 ml/100 g of body weight. This combination of NO-synthase inhibitor with hypertonic solution provides RAAS activation, aldosterone discharge, retention of sodium and water, functional impairment of the vascular endothelium.

Experimental model was based on the use of N-ω-nitro-L-arginine methyl ester, hydrochloride ($C_7H_{15}N5O_4 \times HCl$, M.w. 269.7 [Sigma-Aldrich, USA]) and of sodium chloride (Reachim, Russia).

The solution of inhibitor was prepared in the purified water, 250 mg per 100 ml of 3% sodium chloride. Weighing of the reagents was performed on the analytical balance GH-300 (A&D, Japan).

Animals and their Management, Experimental Groups

The management of the laboratory animals was organized in accordance with the "Sanitary rules of organization, furnishing and management of experimental biological clinics (vivaria)" (RF, approved on 6 Apr. 1973), "Guide for the Care and Use of Laboratory Animals" (USA, National Academy Press, Washington, D.C., 1996); "Guidelines on the Management and Use of Laboratory Animals" (FELASA, 2010), "Laboratory animals" (regulation and guideline, Russian Academy of Medical Sciences, Moscow, 2003).

The experiments were performed with the use of 40 white male Wistar rats with the baseline body weight 220-240 g and 20 white virgin female rats 180-200 g. The animals were purchased from Rappolovo farm (Russian Academy of Medical Sciences, Saint-Petersburg). Besides mixed fodder, the rats received bread.

The duration of adaptation period (acclimatization) was 14 days for each animal. During isolation period, the animals were examined daily (behaviour and general condition), two times in the day, the animals were assessed in the cages (morbidity and mortality). Prior to the experiment, the animals that met the eligibility criteria, were randomly allocated into study groups. Ineligible animals were excluded from the study during the isolation period.

Animal cages were placed into the separate rooms. The control of environment was performed daily during the study. This control included temperature and humidity control. Light period included 12 hours of night plus 12 hours of day (artificial light of fluorescent lamps). The air temperature was maintained at the level of 20-22° C., relative humidity at the level of 50-70%. The air exchange regimen provided about 15 room volumes per hour, $CO_2$ level not more than 0.15% v/v, ammonium level not more than 0.001 mg/L.

During the study, each animal was daily examined. The examination included the assessment of general behaviour and of general condition. Every animal was labelled with the use of picric acid on the fur (rats). The data were recorded in the laboratory logs.

AS-6 substance (lot 080909) containing 101.0% of the active ingredient was used, according to the Protocol of Analysis No. 80-Pr, dated by 25 Sep. 2009 (Federal State Unitary Enterprise Special Technology and Construction Bureau "Tekhnolog"). The substance was used for preparation of solutions for daily oral administration based on the physiological saline.

The physiological saline was used as placebo. The solutions were administered daily through the atraumatic metallic feeding tube with fire-polished olive with the use of dosing syringe.

The animals were divided into the arms as follows: 1—intact animals; 2—control group, males (L-NAME+NaCl; physiological saline as placebo); 3—male rats that received AS-6 in the dose 0.5 mg/kg (Dose 1); 4—male rats that received AS-6 in the dose 5 mg/kg (Dose 2); 5—male rats that received AS-6 in the dose 10 mg/kg (Dose 3); 6—virgin female rats (only in the assessment of the sexual activity). Each group included 8 animals.

Materials and Methods Used to Assess the Functional Parameters of the Cardiovascular Functions The measurement of the blood pressure in rats was performed with the use of the system for non-invasive blood pressure measurement for small animals within the complex Polygraph for electrophysiological studies (MP150WSW "BIOPAC Systems, Inc.", USA.)

Procedure

Rats were placed into special boxes. HR and BP (SBP and DBP) were recorded several minutes after the stabilization of the measured parameters. The parameters were measured on the tails with the use of piezoelectric probe and corresponding cuff, several minutes following animal placement on the thermostated sheet that maintained the temperature in the chambers within 26-27° C. The functional cardiovascular testing was performed before (at baseline) and after the administration of NOS inhibitor and at the end of treatment.

Materials and Methods Used to Assess the Functional Parameters of Endothelium

Biochemical parameters were assessed with the use of prearranged kits (USCN Life Science Inc., USA, Bender MedSystems GmbH, Austria, R&D Systems, USA). The measurement was performed with the use of multifunctional photometer Synergy-2 (BioTek Instruments, Inc., USA). All studies were conducted in compliance with current laboratory regulations [12-13].

The assessment of endothelin-1, vascular endothelial growth factor and nitric oxide levels was performed in the rats' serum at the end of experiment with the use of immuno-enzyme analysis and spectrophotometric analysis with species-specific (rat-specific) antibodies.

Quantitative measurement of endothelin-1 (ET-1) was performed with the use of ELISA with USCN Life Science Inc. (USA) kits. Serum samples of the experimental animals (50 mcL) and standards of known concentrations were introduced into the plate wells. Then, 50 mcL of detecting solution (reagent A) were introduced. After 1-hour incubation at 37° C., the wells were 3-fold rinsed, and 100 mcL of detecting solution (reagent B) were introduced into each well. Thereafter, the plate was incubated again at 37° C. for 30 minutes. The plate was rinsed with washing buffer 5 times, and 90 mcL of TMB substrate were introduced into each well. After 15-minute incubation at 37° C., 50 mcL of stop-solution were added. The reaction was read at 450 nm. The diagrams of dependence of absorption vs. analyte concentration and the parameters of the equation are shown in the FIG. 1 and in the Table 1.

TABLE 1

Parameter of the equation of endothelin concentration dependence

| Curve Name | Curve Formula | A | B | C | D | R2 |
|---|---|---|---|---|---|---|
| ET-1 | $Y = (A - D)/(1 + (X/C)^B) + D$ | 3.93 | 1.03 | 9.25 | 0.0328 | 0.995 |

Figure 2:
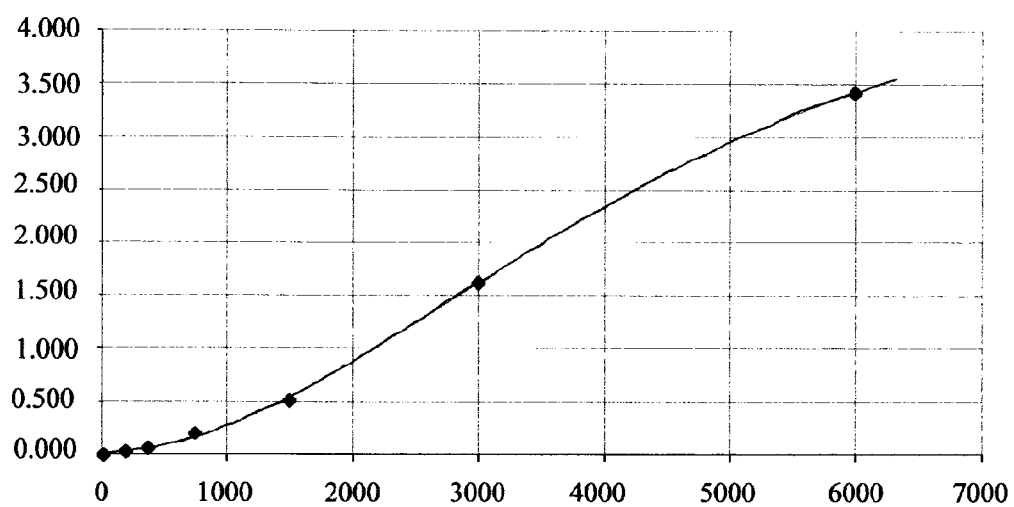
FIG. 2—Dependency diagram of vascular endothelial growth factor (VEGF) absorption vs. analyte concentration in rats.

Quantitative measurement of vascular endothelial growth factor (VEGF) was performed with the use of ELISA with Bender MedSystems GmbH (Austria) kits. Calibration solution 100 mcL, serum samples of the experimental animals (50 mcL) and sample diluent (50 mcL) were introduced into the plate wells. Then, 50 mcL of biotin conjugate were added. After 2-hour incubation at 20° C., the wells were 6 time rinsed, and 100 mcL of streptavidin/horseradish peroxidase conjugate were introduced into each well. Thereafter, the plate was incubated again at 37° C. for 1 hour. The plate was 6 times rinsed with washing buffer, and 100 mcL of TMB substrate were introduced into each well. After 30-minute incubation at 20° C., 100 mcL of stop-solution were added. The reaction was read at 450 and 620 nm. The diagrams of dependence of absorption vs. analyte concentration and the parameters of the equation are shown in the FIG. 2 and in the Table 2.

TABLE 2

Parameters of the equation of VEGF concentration dependence

| Curve Name | Curve Formula | A | B | C | D | E | R2 |
|---|---|---|---|---|---|---|---|
| VEGF | $Y = (A - D)/(1 + (X/C)^B)^E + D$ | 0.0209 | 1.86 | 1.60E+04 | 4.27 | 10.8 | 1 |

Figure 3:
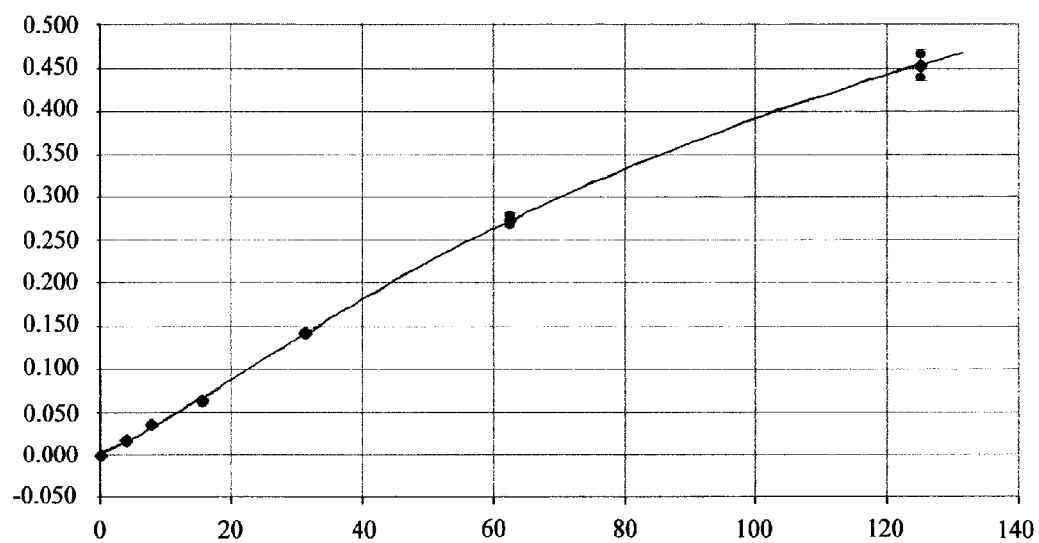
FIG. 3—Dependency diagram of free nitric oxide (NOx) absorption vs. analyte concentration.

Quantitative measurement of unbound nitric oxide was performed with the use spectrophotometry with R&D Systems kits (USA). The proteins were precipitated with zinc sulphate/sodium hydroxide. Serum supernatant samples of the experimental animals (50 mcL) and standards of known concentrations were introduced into the plate wells. Then, 50 mcL of sample diluent, Griss reagent 1 and Griss reagent 2 were added. The reaction was read at 540 and 690 nm after 10-minute incubation at 37° C. The diagrams of dependence of absorption vs. analyte concentration and the parameters of the equation are shown in the FIG. 3 and in the Table 3.

TABLE 3

Parameters of the equation of NO concentration dependence

| Curve Name | Curve Formula | A | B | C | D | R2 |
|---|---|---|---|---|---|---|
| NOx | $Y = (A - D)/(1 + (X/C)^B) + D$ | 0.00145 | 1.23 | 125 | 0.904 | 1 |

Materials and Methods Used to Assess the Sexual Activity

Testing of the animals' sexual activity was performed after the end of treatment cycle. Tested male was placed into the testing chamber (40×40×30 cm), 5 minutes before the presentation of sexually receptive female rat. One female was placed next to each male. The assessment of sexual behaviour was performed in the dark room at blind red light. The components of sexual activity were visually recorded during a 30-minute period: mounting latency (ML—interval from the female placing into the cage to the first male mounting) and the rate of mountings, intromissions and ejaculations [14-15].

Materials and Methods Used in the Data Statistical Processing

The data of observation recorded into the laboratory logs, measurement data and instruments recordings obtained during testing of physiological and biochemical parameters were introduced into the primary data matrix in Microsoft Excel 2003. A multilevel table was composed, with animals distributed in accordance with the numbers and corresponding drug doses.

The statistical analysis of the results was performed using Statistica 8.0 software package. First of all, the values were checked for the normality of distribution (Shapiro-Wilk test). Based on this check, the results were not normally distributed. Therefore, non-parametric tests were used, i.e. Kruskal-Wallis rank dispersion test. The significance level was 0.05 for each analysis.

Study Results

Effect of Azasidnon on the Blood Pressure in Rats in the Model of Hypertension with Endothelial Dysfunction The effects of different doses of AS-6 on the cardiovascular parameters of rats in the model of arterial hypertension with endothelial dysfunction are shown in the Table 4.

TABLE 4

Effect of Azasidnon on the blood pressure parameters in rats

| Study | Baseline (Day 0) | | | Post-dose L-NAME (Day 7) | | | After treatment (Day 14) | | |
|---|---|---|---|---|---|---|---|---|---|
| arms (n = 8) | SBP | DBP | HR | SBP | DBP | HR | SBP | DBP | HR |
| Naive | 128.4 ± 6.4 | 96.2 ± 5.4 | 429.1 ± 13.5 | 126.1 ± 3.4 | 91.1 ± 3.3 | 400.5 ± 11.8 | 124.6 ± 3.7 | 96.1 ± 2.4 | 390.6 ± 6.2 |
| Control | 128.1 ± 6.4 | 99.6 ± 4.8 | 397.1 ± 15.0 | 149.0 ± 2.7 */** | 111.0 ± 6.2 | 358.6 ± 6.7 | 145.4 ± 4.4 */** | 109.8 ± 9.1 | 389.8 ± 13.4 |
| AS-6 0.5 mg/kg | 126.2 ± 2.5 | 98.7 ± 2.2 | 417.6 ± 17.6 | 145.0 ± 3.1 */** | 113.8 ± 4.6 */** | 351.8 ± 8.7 | 153.1 ± 7.3 */** | 111.9 ± 5.2 */** | 420.0 ± 13.7 |
| AS-6 5 mg/kg | 123.8 ± 3.4 | 97.9 ± 3.2 | 428.2 ± 22.1 | 148.6 ± 4.5 */** | 117.0 ± 4.4 */** | 376.0 ± 15.3 | 141.9 ± 7.1 ** | 111.5 ± 7.9 | 435.9 ± 28.9 |
| AS-6 10 mg/kg | 130.5 ± 4.6 | 98.5 ± 4.7 | 393.6 ± 19.1 | 149.1 ± 3.4 */** | 120.1 ± 5.0 */** | 357.1 ± 14.8 | 123.4 ± 4.2 | 102.0 ± 3.2 | 404.4 ± 17.6 |

Table 4 notes:
\* p < 0.05, significant difference vs. naive animals.
\*\* p < 0.05, significant difference vs. baseline.

The experimental model showed increased systolic blood pressure by 20 mm Hg on the average and increased diastolic BP by 10 mm Hg on the average. AS-6 provided dose-dependent decrease of blood pressure, with the peak at 10 mg/kg after 7 days of treatment. No significant changes of the heart rate were observed either in the control or experimental arm.

AS-6 in the dose 0.5 mg/kg did not affect SBP or DBP levels in (p>0.05=1). With 10-fold dose increase up to 5 mg/kg the decrease of elevated DBP and unchanged elevated SBP were observed (p<0.05). AS-6 in the dose 10 mg/kg provided normalization of the blood pressure vs. baseline values and experimental model (significant difference, p<0.05).

Effect of AS-6 on the Endothelial Dysfunction Parameters

The parameters that characterize endothelial state in the model of arterial hypertension with endothelial dysfunction vs. Azasidnon doses are shown in the Table 5.

mg/kg: p=0.010 vs. control animals and p=0.015 vs. 1 dose of AS-6 0.5 mg/kg). Moreover, the dose-dependent trend to the normalization of vascular endothelial growth factor production was observed (10 mg/kg dose: p=0.116 vs. control male rats).

During AS-6 administration, the dose-dependent increase of nitric oxide (NO) production was observed, which exceeded the level of treatment-naive animals at the dose of AS-6 10 mg/kg (p=0.0024 vs. intact male rats; p=0.0000 vs. control group; p=0.058 vs. 0.5 mg/kg and 5 mg/kg doses).

The analysis of the data obtained led to a conclusion about AS-6 being an indirect nitric oxide donator in the animals (in vivo), as far as this was associated with significant changes of the detectable serum level of nitrites. Moreover, it is an endothelial protector that provides normalization of endothelin production and the trend to normalization of vascular endothelial growth factor in rats.

TABLE 5

AS-6 effect on the endothelial parameters

| Study parameters | Study arms (n = 8; M ± m) | | | | |
|---|---|---|---|---|---|
| | Naive | Control | AS-6, 0.5 mg/kg | AS-6, 5.0 mg/kg | AS-6, 10.0 mg/kg |
| ET-1, pg/mL | 1.28 ± 0.22 | 3.45 ± 0.72* | 2.48 ± 0.50 | 1.75 ± 0.48 | 0.78 ± 0.29^# |
| VEGF, pg/mL | 123.33 ± 31.97 | 41.66 ± 5.34 | 46.01 ± 2.42 | 79.49 ± 19.75 | 91.95 ± 21.84 |
| NO, mcmol/l | 9.61 ± 0.58 | 5.26 ± 0.51* | 8.83 ± 1.06 | 10.75 ± 0.55^ | 14.08 ± 1.25*^ |

Table 5 notes:
\*p < 0.05, significant difference vs. naive animals;
^p < 0.05, significant difference vs. control animals;
p < 0.05, significant difference vs. AS-6 0.5 mg/kg arm.

Following administration of hypertonic saline and NO-synthase inhibitor, the control animals demonstrated the impairment of vascular endothelium associated with significant and relevant hyperexpression of endothelin-1, main vasoconstrictor (p=0.0201 vs. treatment-naive male rats), depressed production of NO, vascular endothelial relaxation factor (p=0.0000 vs. treatment-naive male rats), and a trend to the decreased production of vascular endothelial growth factor (VEGF) (p=0.071 vs. treatment-naive male rats).

Treatment with AS-6 resulted in a significant favourable changes of endothelin-1 levels (the most significant changes were observed following AS-6 use in the maximum dose 10

Effects of Azasidnon on the Sexual Activity in Male Rats

The study results are summarized in the Table 6.

The control males demonstrated decreased measures of sexual activity compared to the naive animals. Most animals demonstrated 1 episode of sexual activity during the study. In these rats, the interval between the sexual activity sessions showed non-significant accrual compared to the naive animals. In the control group, intromissions were only observed in 12% of males. At the same time, among the naive animals, 2 sessions of sexual activity were observed; 25% of them demonstrated intromissions.

TABLE 6

Effect of Azasidnon on the sexual behaviour in male rats

| Study parameters | Study arms (n = 8; M ± m) | | | | |
|---|---|---|---|---|---|
| | Naive | Control | Azasidnon 0.5 mg/kg | Azasidnon 5.0 mg/kg | Azasidnon 10.0 mg/kg |
| Muzzling, licking of the females | + | + | + | + | + |
| Mounting rate | 4.4 ± 1.5 | 2.4 ± 0.5 | 6.6 ± 2.8 | 7.4 ± 3.1 | 8.6 ± 2.6 |
| Intromission rate | 0.4 ± 0.3 | 0.1 ± 0.1 | 1.6 ± 1.4 | 1.4 ± 1.1 | 3.1 ± 1.5 |
| Ejaculation rate | − | − | − | − | − |
| Mounting latency, min | 11.3 ± 1.0 | 8.7 ± 1.2 | 3.9 ± 0.9*^ | 4.2 ± 1.9*^ | 3.2 ± 1.4*^ |
| Intersession interval, min | 10.6 ± 1.2 | 15.0 ± 1.0 | 8.8 ± 0.9 | 10.2 ± 2.2 | 7.5 ± 1.9 |

Notes
*$p < 0.05$, significant difference vs. naive animals;
^$p < 0.05$, significant difference vs. control animals;
+ - present;
− - absent.

AS-6 animals (all study doses) demonstrated activation of any parameters of impaired sexual behaviour: increased mounting and intromission rate, significant reduction of mounting latency. In these rats, the interval between the sexual activity sessions was similar to the naive animals.

AS-6 0.5 and 5 mg/kg led to the increased mounting rate vs. control in 40% of animals, to increased intromission rate in 25% of rats and to 1.5-fold decrease of ML.

The most significant treatment effect in relation to the study parameters was observed in the animals that received the dose 10 mg/kg. The number of animals with intromissions increased to 50% (in naive rats) and to 25%—among the animals that received the doses 0.5 and 5 mg/kg. Decreased mounting latency compared to the naive and control animals and the trend to the decreased intersession interval were demonstrated.

AS-6 did not influence such parameter of sexual function as ejaculation. Within the given methodological conditions of the study of sexual activity, this characteristic was absent both in the control and experimental males, and in the naive rats.

Thus, AS-6 provided decreased mounting latency and non-significant increase of mounting rate. The maximum effect was observed following administration of 10 mg/kg of AS-6, which contributed to the increased number of animals with intromissions (4-fold increase vs. control), increased rate of the sexual activity sessions, decreased mounting latency and inter-mounting interval.

The pharmacological activity of AS-6 substance was studied in the model of arterial hypertension with endothelial dysfunction at the Drug Toxicological Laboratory. The dose-dependent activity of the substance was demonstrated, as well as endothelial protection due to the normalization of endothelin-1 production and increased level of nitric oxide at the background of inhibition of endothelial NO-synthase induced by L-NAME.

No dose dependency was demonstrated in the influence on the sexual activity of males. The increased sexual activity (decreased mounting latency, reduced interval between copulation sessions, increased intromission rate) was recorded.

The data obtained led to a conclusion about the potential of using the oxatriazolium-5-olate derivatives in the treatment of sexual disorders, such as: absence or loss of sexual desire, insufficient genital reaction, orgasmic dysfunction.

REFERENCES

1. Ageev, F. T., Ovchinnikov, A. G, Mareev, V. Yu., Belenkov, Yu. N. Endothelial dysfunction and heart failure: pathogenetic relations and possibility of treatment with the use of angiotensin-converting enzyme//Consilium medicum, volume 3, No. 2, 2001.—media/consilium/01_02/61.shtml:: sunday, 22 Apr. 2001 15:01:07
2. Startoseltseva, O. A. Use of pharmacological preconditioning with Nicorandil . . . Author's dissertation abstract . . . Candidate of Medical Sciences, Kursk.—2012.
3. Patent RU 2351328 C1 (Limited Liability Company Consortium-PIK), 10 Apr. 2009.
4. Bivalacyna T. I., Usta M. F., Champion H. C. et al.//I. Androl.—2003.—V.24, No. 6.—P. 17-37.
5. Solomon H., Man J. M., Jackson G//Heart.—2003.—V. 89.—P. 251-253.
6. Pyrochkin, V. M., Mironchik, E. V. Erectile dysfunction: new symptom for cardiologist?//Meditsinskie novosti. No. 10, 2010.—www.mednovosti.by.
7. International application WO 2013100340 A1 (JEONNAM BIOINDUSTRY FOUNDATION), 4 Jul. 2013.
8. US application US 2012277200 A1 (EMOTIONAL BRAIN BV), 1 Nov. 2012.
9. International application WO 2011161655 A1 (HORPHAG RES IP PRE LTD et al.), 29 Dec. 2011.
10. T. L. Thomas, M. Fedorchuk, B. V. Shetty, E. E. Amderson. <<The Synthesis and Activity of Some 3-Substituted 1,2,3,4-Pseudooxatriazol-5-ones and Their Precursors and Related Compounds>>//Pennwalt Corporation, Pharmaceutical Division, Department of Organic Chemistry, Rochester, N.Y., 11.08.1969.
11. Mary Q. Lurid, Lemont B. Kier, Richard A. Glennon, John L. Egle, Jr. <<Preliminary Studies of Mesoionic 3-(Substituted-aryl)-ψ-oxatriazoles as Potential Antihypertensive Agents>>//Department of Pharmaceutical Chemistry, School of Pharmacy, and Department of Pharmacology, Medical College of Virginia, Virginia Commonwealth University, Richmond, Va. 23298, 12.04.1982.
12. Medical laboratory technologies. Volume 2. Prof. A. I. Karpishchenko (ed.)—SPb: Intermedica, 2002, −600 pp.
13. Menshikov, V. V. Clinical laboratory analytics: vol. 1, vol. 2. Special analytical technologies in the clinical laboratory.—M.: Labirinform—RAMLD, 1999. 352 pp., in 2 vol.

14. Bairamov, A. A., Zaichenko, I. N., Bogdanovca, L. A., Sapronov, N. S. Role of cholinergic pathways in the regulation of sexual activity in the acute and chronic stress// Farmakologiya, Vol. 7, 2006. P. 18-28.

15. Buresh, Ya., Bureshova, O., Houston, D. P. Methods and main experiments in the studies of brain and behaviour./ Batuev, A. S. (ed.).—M.: Vysshaya shkola, 1991. 399 pp.

16. Glanz S. Medico-biological statistics.—M.: Praktika, 1998. 459 pp.

17. Statistics: Statistica 6.0 (Company guideline) StatSoft, 1999. 3756 pp.

The invention claimed is:

1. A method of treating one or more sexual disorders in a subject, the method comprising administering to the subject a therapeutically effective amount of a pharmaceutical composition comprising 3-(3-[1,2,4]-triazolo)-oxatriazolium-5-olate.

2. The method according to claim 1, wherein the one or more sexual disorders are selected from the group consisting of absence of sexual desire, loss of sexual desire, insufficient genital reaction, or orgasmic dysfunction.

* * * * *